United States Patent [19]
Vecere

[11] Patent Number: 5,218,874
[45] Date of Patent: Jun. 15, 1993

[54] FITTING AND TUBE APPARATUS FOR GAS EMISSION SAMPLE CONTAINER

[76] Inventor: William T. Vecere, 2013 Roman Ct., Warren, Mich. 48092

[21] Appl. No.: 921,355

[22] Filed: Jul. 27, 1992

Related U.S. Application Data

[60] Continuation of Ser. No. 781,729, Oct. 23, 1991, abandoned, which is a division of Ser. No. 574,078, Aug. 29, 1990, Pat. No. 5,074,155.

[51] Int. Cl.⁵ .............................................. G01N 1/14
[52] U.S. Cl. .................................................. 73/864.62
[58] Field of Search ........................... 73/23.31–23.33, 73/864, 864.33, 864.51, 864.62–864.64, 864.91, 863.81, 863.83, 863.86, 864.01, 864.21, 864.81, 864.86, 864.87, 864.62; 383/109, 3, 904, 906

[56] References Cited

U.S. PATENT DOCUMENTS

| | | | |
|---|---|---|---|
| 3,332,415 | 7/1967 | Ericson | 383/3 |
| 3,357,632 | 12/1967 | Stanforth | 383/3 |
| 3,603,155 | 9/1971 | Morris et al. | 73/421.5 R |
| 3,759,667 | 9/1973 | Bannister et al. | 63/864.22 |
| 3,977,708 | 8/1976 | Jopp | 285/342 |
| 4,546,659 | 10/1985 | Gill et al. | 73/864.62 |
| 4,548,321 | 10/1985 | Mockesch et al. | 383/109 |
| 4,700,531 | 10/1987 | Hsu et al. | 383/109 |
| 4,718,778 | 1/1988 | Ichikawa | 383/109 |
| 4,772,134 | 9/1988 | Jensen et al. | 383/906 |
| 4,817,423 | 4/1989 | Christiansen | 73/153 |
| 4,887,472 | 12/1989 | Jansen | 73/863.86 |
| 4,893,731 | 1/1990 | Richter | 222/105 |

FOREIGN PATENT DOCUMENTS 1249717 9/1967 Fed. Rep. of Germany ...... 383/906

*Primary Examiner*—Robert Raevis
*Attorney, Agent, or Firm*—Basile and Hanlon

[57] ABSTRACT

A fitting for a sealed gas emission sample container with an aperture includes a body having planar top and bottom portions and top and bottom surfaces curving smoothly away from the top and bottom portions, respectively, to a peripheral edge. Gas ports are formed in the body extending radially inward from the peripheral edge of the body and are disposed in fluid flow communication with a central bore formed in and extending through the top portion of the body. A coupling is mounted in the central bore in the body for connecting the fitting to a source of gas emissions and gas emission test equipment. Hollow conduits having spaced apertures formed along their length are connected at opposed ends to the gas flow ports. The sealed container is formed of single-ply top and bottom flexible sheets sealed at their peripheral edges or, in another embodiment, two separate top sheets and two separate bottom sheets, all of which are sealed together at their peripheral edges.

3 Claims, 2 Drawing Sheets

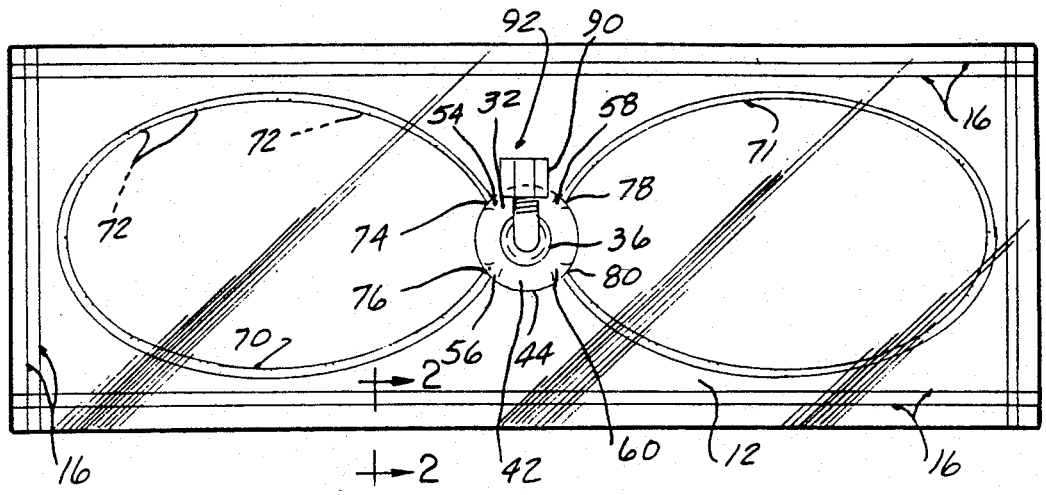
FIG-1
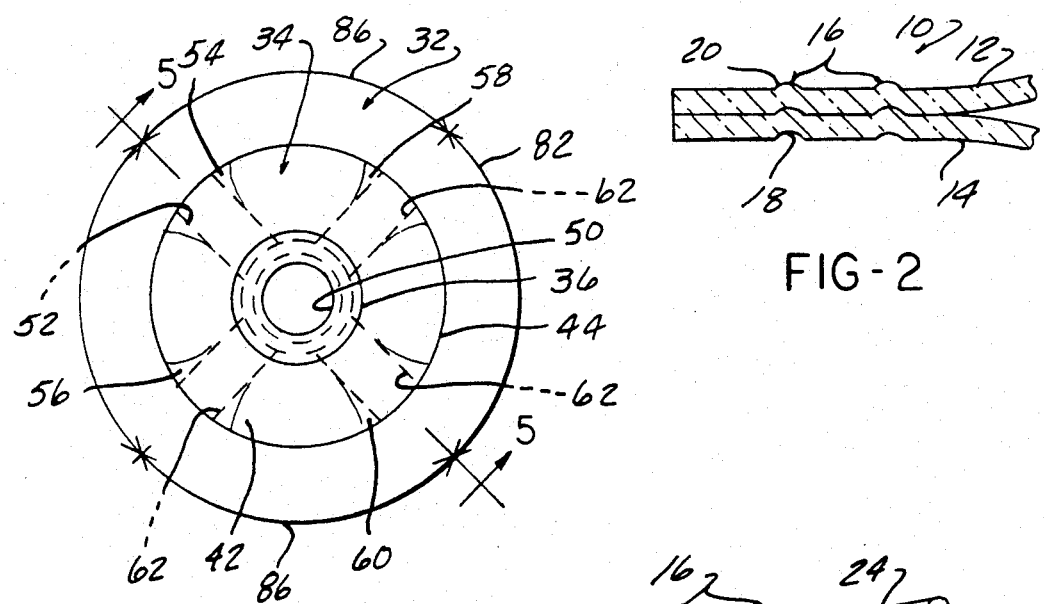
FIG-4
FIG-2
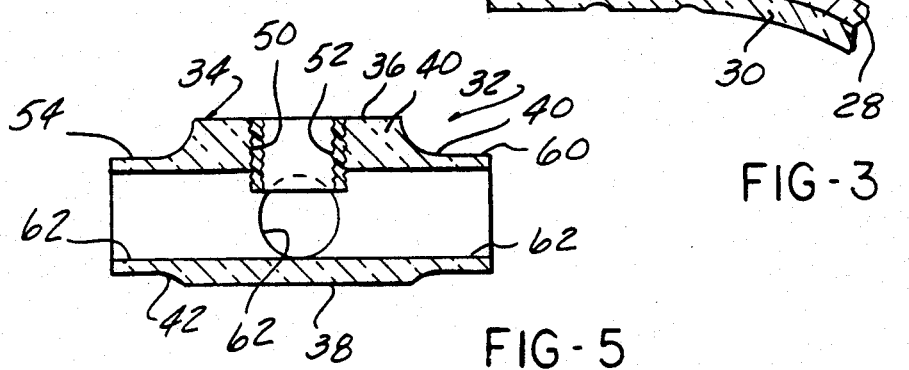
FIG-5
FIG-3

FITTING AND TUBE APPARATUS FOR GAS EMISSION SAMPLE CONTAINER

CROSS REFERENCE TO CO-PENDING APPLICATION

This application is a continuation of application Ser. No. 07/781,729, filed Oct. 23, 1991, now abandoned, which is a division application of copending U.S. patent application Ser. No. 07/574,078, filed on Aug. 29, 1990, now U.S. Pat. No. 5,074,155, issued Dec. 24, 1991, in the name of William T. Vecere and entitled "Fitting and Tube Apparatus for Gas Emission Sample Container".

BACKGROUND OF THE INVENTION

1. Field of the Invention

The present invention relates to gas emission sample containers for collecting gas emissions from motor vehicles and, more specifically, to fittings and tube apparatus for use in such gas emission sample containers.

2. State of the Art

Expandable, sealed containers or bags are employed for collecting and temporarily storing gas emissions from motor vehicles before the collected emissions are analyzed by suitable test equipment. Such containers are expandable to a constant volume to collect a known quantity of gaseous emissions.

Typically, a plurality of such containers, such as six containers, are connected through suitable conduits, valves, etc., to a test apparatus to collect separate quantities of gas emissions from a vehicle and from ambient atmosphere. Samples of emissions from a motor vehicle under test are collected in the sealed containers as the motor vehicle is operated according to a prescribed test schedule corresponding to various engine operating conditions.

The expandable containers include a fitting sealingly mounted in each container which is connected to the test apparatus to receive gas emissions from the vehicle under test. The fitting directs the gas emissions into the container for storage, as well as enabling the stored gas contents to be evacuated for subsequent analysis. The fitting and the sealed container are made of a chemically inert material, such as a fluorinated carbon plastic, i.e., plastics sold under the registered trademarks TEFLON and/or TEDLAR.

In order to prevent wrinkling of the container when evacuated of gas and to insure complete inflation of the container to a constant volume without internal dead spots, small diameter, hollow conduits or tubes are disposed within the sealed container and connected in fluid flow communication with the fitting. The conduits have apertures formed along their lengths to draw gas from different parts of the container to prevent stratification of the gas within the container and to insure thorough mixing of the gas. Such conduits have been provided in a variety of shapes, such as a plurality of circumferentially spaced, straight segments, curved segments, etc.

However, the fittings employed in such gas emission sample containers have heretofore had a generally spherical shape with internal bores connected in fluid flow communication with a port having an externally mounted hollow connector attached thereto. It is felt by those in the industry that the size of the spherical-shaped fitting and the relatively large diameter of the tubes disposed within the sealed container create dead spots in the container adjacent the fitting which prevents complete inflation of the container and/or complete evacuation of the gas from the container. This leads to erroneous emission test results since the quantity of gas varies from container to container.

Thus, it would be desirable to provide a fitting and tube apparatus for a gas emission sample container which overcomes the above-described problems associated with prior art fitting and tube apparatus. It would also be desirable to provide a fitting and tube apparatus for a gas emission sample container which substantially eliminates dead spots within the container during the inflation and evacuation of the sealed container. It would also be desirable to provide a fitting and tube apparatus for a gas emission sample container which effectively prevents stratification of the gas within the container by drawing gas equally from all parts of the sealed container. It would also be desirable to provide a fitting and tube apparatus for a gas emission sample container which minimizes wrinkling of the sealed container when empty thereby reducing fatigue of the container and enabling more tests to be performed using the same container. Finally, it would be desirable to provide a gas emission sample container which may be constructed of thinner, flexible sheets, while at the same time providing the desired sealing features of previously devised containers.

SUMMARY OF THE INVENTION

The present invention is a fitting and tube apparatus for a gas emission sample container. The gas emission sample container includes a sealed, expandable body having an aperture formed in one wall. The fitting comprises a body having a circular plan shape with substantially planar top and bottom portions. Top and bottom surfaces are formed on the body and curve smoothly away from the top and bottom portions and terminate in a common peripheral edge.

A bore is formed in the body and extends through the top portion of the body into the interior of the body. A plurality of gas flow ports are formed in the peripheral edge of the body and are disposed in fluid flow communication with the bore in the body.

Hollow gas conduit means are connected to the body through the gas flow ports and are disposed in fluid flow communication with the bore in the body. A plurality of spaced apertures are formed in the gas conduit means, the apertures connecting the hollow gas conduit means in fluid flow communication with the interior of the sealed container.

A hollow coupling is sealingly attached to the bore in the body and is connectible to test apparatus to supply gas emissions to the sealed emission container wherein the sealed container expands to temporarily store such gas emissions, as well as to evacuate the stored gases from the container for subsequent analysis.

The fitting, gas conduits and the sealed container are formed of a chemically inert plastic. Further, the gas flow ports are arranged on the body of the fitting in pairs at predetermined circumferential angular spacings between each port and between each pair of ports to form a predetermined shape for the gas conduit means which are connected at each of two ends to one pair of gas ports. In a preferred embodiment, two ports in each pair of ports are spaced 70° apart. Each port in each pair of ports is spaced from an adjacent port in the other pair of ports by an angle of 110°. This forms each gas conduit means into an elongated, substantially tear-drop shape which covers a substantial portion of the interior of the sealed container. Other angular configurations for the gas flow ports are also possible to provide different shapes for the gas conduit means connected to each pair of ports depending on the shape and size of the sealed container and application requirements.

In one embodiment, the sealed container is formed of single-ply top and bottom plastic sheets. For example, 4 mil. plastic sheet is employed and sealingly connected at the peripheral edges of the top and bottom sheets to form the sealed container. In other embodiment, the container is formed of two pairs of thinner flexible sheets, i.e., two upper sheets and two lower or bottom sheets, all of which are sealingly connected at their peripheral edges to form the sealed container. The multiple-ply or thickness construction of the sealed container enables smaller thickness sheets to be employed while at the same time providing the necessary sealing characteristics for the sealed gas emission container.

The fitting of the present invention has a smooth, flat shape. This shape prevents wrinkling of the container adjacent the fitting when the container is evacuated of gas and the formation of dead spots which could lead to inaccurate test results due to changes in the volume of the container during inflation and evacuation.

The orientation of the gas ports on the fitting provides specific shapes for the gas flow conduits connected to the fittings which also prevents wrinkling of the container when the container is evacuated, as well as providing complete inflation of the container to a constant volume. Since the gas conduits extend over a large portion of the sealed container, stratification of the gas, as encountered in previously devised containers, is minimized since the gas is withdrawn evenly from all portions of the container.

Furthermore, the construction of the sealed container from multiple thicknesses of flexible plastic sheet enables such a container to be constructed of smaller thickness sheets, while at the same time providing the desired gas sealing characteristics.

BRIEF DESCRIPTION OF THE DRAWING

The various features, advantages and other uses of the present invention will become more apparent by referring to the following detailed description and drawing in which:

FIG. 1 is a plan view of a fitting and tube apparatus of the present invention mounted in a sealed gas emission sample container;

FIG. 2 is a cross sectional view generally taken along line 2—2 in FIG. 1;

FIG. 3 is a cross sectional view, generally similar to FIG. 2, but showing an alternate embodiment of the sealed gas emission sample container;

FIG. 4 is an enlarged, plan view of the fitting shown in FIG. 1;

FIG. 5 is a cross sectional view generally taken along line 5—5 in FIG. 4;

DESCRIPTION OF THE PREFERRED EMBODIMENTS

Figure 7:
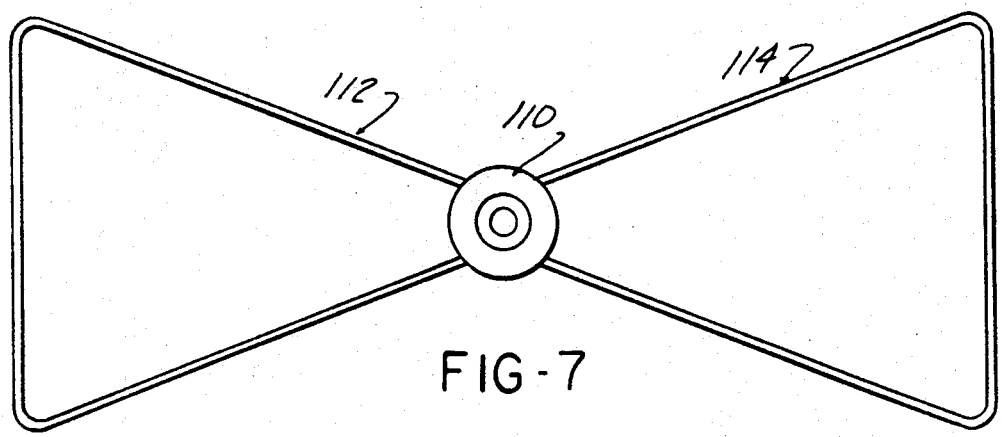
FIG. 7 is a plan view of an alternate embodiment of the fitting and tube apparatus of the present invention.

Referring now to the drawing, and to FIG. 1 in particular, there is illustrated a gas emission sample container 10 which is connectible to suitable test equipment, not shown, to collect and temporarily store gas emissions from a motor vehicle prior to the evacuation of such stored gas emissions for subsequent analysis.

As shown in FIGS. 1 and 2, the gas emission sample container 10 comprises a sealed enclosure of any shape, such as rectangular, square, circular, etc. It will be understood that a rectangular shape for the container 10 is illustrated by way of example only. Further, the container 10 may be provided in different sizes depending upon the requirements of a particular test application.

The sealed container or bag 10, in one embodiment, is formed of two flexible sheets of chemically inert material. Preferably, fluorinated plastics chosen from the fluorocarbon family, such as those sold under the trademarks TEFLON, TEDLAR and HALON, may be employed. In one embodiment, as shown in FIG. 2, the sealed container 10 is formed of an upper sheet 12 and a lower or bottom sheet 14 of a single thickness or ply. Typically, the single ply sheets 12 and 14 are 2 or 4 mils. in thickness. The upper and bottom sheets 12 and 14, respectively, are sealingly connected at their peripheral edges by any suitable means, such as by the depicted heat seam 16. Such a sealing method forms a recess 18 on one side of the joined sheets 12 and 14 and a small projection or bump 20 on the opposite surface. For additional sealing capability, two spaced heat seams 16 may be employed about the peripheral edges of the upper and bottom sheets 12 and 14. The seam or seams 16 seal the peripheral edges of the upper and bottom sheets 12 and 14 and form a hollow, expandable cavity 22, FIG. 6, within the interior of the sealed container 10.

In an alternate embodiment, shown in FIG. 3, the sealed container 10 is formed of two pairs of upper sheets 24 and 26 and lower or bottom sheets 28 and 30. The upper and bottom sheets 24, 26, 28 and 30 are sealingly joined together at their peripheral edges by any suitable means, such as by a heat seam or seams 16. The use of pairs of upper and lower sheets enables the use of thinner sheets, i.e., 2 mils., but with the same sealing characteristics.

Figure 6:
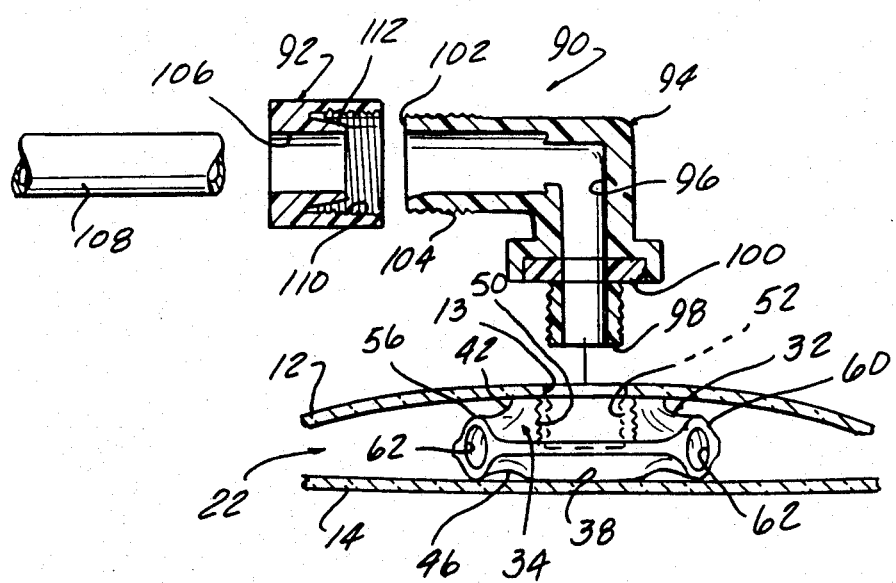
FIG. 6 is a partial, exploded, front elevational view showing the mounting of the fitting within the sealed container and the attachment of the coupling to the fitting.

A fitting 32, as shown in FIG. 1, and in greater detail in FIGS. 4, 5 and 6, is mounted within the sealed container 10 for controlling the flow of gas emissions to and from the interior 22 of the sealed container 10, as described in greater detail hereafter. The fitting 32 comprises a body 34 formed of a chemically inert material. Any suitable material, such as a fluorocarbon or fluorinated plastic may be employed. By way of example, fluorocarbons sold under the trademark TEFLON and those sold under trade or chemical names of TFE, PTFE, FEP, PFA and ECTFE, may be employed. Other fluorocarbonated plastics sold under the trademarks, Flouns, HALON, Halars and Kynar, may be employed. Additionally, polyvinylfluorines, sold under the trademark TEDLAR or trade names PVF and PV2F, may also be employed.

The body 34 of the fitting 32 has a generally circular shape in plan, as shown in FIGS. 1 and 4. The body 32 includes a top portion 36 and an opposed, spaced bottom portion 38, both of generally planar configuration.

The top portion 36 is formed on a boss 40 which extends upward from the main portion of the body 34.

The body 34 has a top surface with walls 42 which curve smoothly from the top portion 36 of the boss 40 radially outward to a peripheral edge or rim 44. Similarly, the body 34 includes a bottom surface in which walls 46 curve smoothly radially outward from the bottom portion 38 to the peripheral edge or rim 44. The peripheral edge or rim 44 is thus spaced between the top and bottom portions 36 and 38, respectively.

A bore 50 is centrally located in the top portion 36 of the body 34 and extends through the boss 40 into the interior of the body 34. The bore 50 may be internally threaded. For additional strength, an internally threaded metallic sleeve 52 is mounted within the bore 50, as shown in detail in FIG. 5.

A plurality of gas flow ports, such as gas flow ports 54, 56, 58 and 60, are formed in the body 34. The gas flow ports 54, 56, 58 and 60 comprise bores, such as bore 62, which extend through the body 34 and are connected in fluid flow communication with the central bore 50 in the body 34, as shown in FIGS. 4 and 5. It should be noted that the top and bottom wall surfaces 42 and 46 of the body 34 taper upward a small amount at the peripheral edge 44 of the body 34 at the location of each of the gas flow ports 54, 56, 58 and 60.

Gas conduit means are disposed within the sealed container 10 and connected to selected ones of the gas flow ports in the fitting 32 to alternately conduct gas supplied through the fitting 32 into the interior 22 of the sealed container 10 and, also, to provide for withdrawal of gas stored within the interior 22 of the container 10 through the fitting 32 to suitable test equipment, as described hereafter.

In a preferred embodiment, the gas conduit means comprises a hollow, flexible tubular member 70, as shown in FIG. 1. By way of example only and not limitation, two gas flow conduits 70 are employed in one embodiment of the present invention. It will be understood that other numbers of gas flow conduits, such as one, three, etc., may also be employed in the sealed container 10 with suitable modification of the fitting 32.

The gas flow conduit 70 comprises a hollow tubular member preferably formed of a chemically inert material, such as those sold under the trademarks, TEFLON or TEDLAR. The gas flow conduit 70 is provided with a plurality of spaced apertures 72 formed in the side walls thereof along the length of the conduit 70, between the first and second ends 74 and 76, respectively. The apertures 72 provide a fluid flow path between the hollow interior of the gas flow conduit 70 and the interior 22 of the sealed container 10.

In a preferred embodiment, two separate conduits 70 and 71 are connected at their respective first and second ends to selected ones of the gas ports in the fitting 32. Thus, the first end 74 of the first gas flow conduit 70 is connected to the gas flow port 54 in the fitting 32. The second end 76 of the conduit 70 is connected to the gas flow port 56. Similarly, the first and second ends 78 and 80 of the second gas flow conduit 71 are respectively connected to the gas flow ports 58 and 60 in the fitting 32. The gas flow ports are thus arranged in associated pairs formed of a first pair of ports 54 and 56 and a second pair of ports 58 and 60. The angular spacing of each of the ports 54, 56, 58 and 60 in the fitting 32 is selected to provide a desired shape and configuration to each of the gas conduits 70 and 71. As shown in FIG. 4, the angular spacing between the ports in each pair of ports, such as between ports 54 and 56, as shown by reference number 82, is substantially 70°. The same spacing, as shown by reference number 82, is provided between the opposed pair of ports 58 and 60. This provides a spacing of substantially 110°, as shown by reference number 86, between a port of each pair of ports and the adjacent port of the opposite pair of ports, such as between ports 54 and 58 or between ports 56 and 60.

This angular orientation of the gas flow ports 54, 56, 58 and 60 in the fitting 32 provides the elongated, substantially tear-drop shape for the gas conduits 70 and 71, as shown in FIG. 1. In this manner, the gas conduits 70 and 71 fill a substantially large portion of the interior 22 of the sealed container 10 so as to enable the interior 22 of the sealed container 10 to be completely filled with gas emissions supplied through the fitting 32 as well as to enable such stored gas emissions to be completely withdrawn from all portions of the sealed container 10.

The fitting 32 is connected to the source of gas emissions and/or emission test apparatus by means of a coupling denoted generally by reference number 90 in FIGS. 1 and 6. The coupling 90 preferably comprises a nut 92 and a hollow body 94. The body 94 is shown as having a generally elbow shape; although a straight shape for the body 94 may also be provided. The body 94 includes a hollow interior bore 96 which extends between opposed ends of the body 94. The first end 98 of the body 94 is provided with a plurality of external threads which are threadingly engageable with the threads in the insert 52 mounted in the central bore 50 in the fitting 32 to attach the body 94 to the fitting 32. A seal means, such as an O-ring 100, is mounted in a recess at the end of the threaded first end portion 98 of the body 94 for sealingly contacting the upper sheet 12 of the sealed container 10 to sealingly connect the body 94 to the sealed container 10 and to sealingly close the aperture 13 in the top sheet 12 of the container 10. The second end 102 of the body 94 is also provided with a plurality of external threads 104.

The nut 92 includes a central, through bore 106 which is adapted to slidingly receive one end of a hollow conduit or tube 108. The conduit 108 is attached at an opposite end to the test equipment for the supply of gas emissions to the apparatus of the present invention and/or to connect such stored gas emissions to test equipment for analysis. The nut 92 may be any conventional nut, such as one disclosed in U.S. Pat. No. 3,977,708 and manufactured by Fluoroware, Inc. The contents of this patent are incorporated herein by reference with respect to the construction of the nut 92.

As shown in FIG. 6, the nut 92 includes a plurality of internal threads 110 which threadingly engage the external threads 104 on the second end 102 of the body 94. Further, the nut 92 includes an internal, elongated, relatively thin sleeve 112. The side walls of the sleeve 112 taper inwardly from one end to a terminal end and are spaced from the opposed threads 110. This arrangement captures the end of the conduit 108 as the nut 92 is threaded onto the second end 102 of the body 94 to sealingly connect the conduit 108 to the body 94.

In use, the sealed container 10 is initially completely evacuated of any contents such that the top and bottom sheets 12 and 14 are substantially in registry and conform to the smoothly curved wall surfaces 42 and 46 on the fitting 32 and about the gas flow conduits 70 and 71. The gas conduit 108, shown in FIG. 6, is connected to a suitable source of gas emissions, such as the engine of a motor vehicle under test. The other end of the conduit 108 is connected to the body 94 after the body 94 has been sealingly threaded to the fitting 32 into sealed engagement with the top sheet 12 adjacent the aperture 13 in the top surface of the top sheet 12.

Then, gas emissions from the motor vehicle are supplied through the conduit 108, the body 94 and the fitting 32 into the hollow gas conduits 70 and 71 and then to the interior 22 of the sealed container 10. The sealed container 10 inflates to a constant volume and, due to the sealed nature of the container 10, retains the gas emissions for a predetermined amount of time.

Subsequently, when it is desired to analyze the contents of the gas emissions stored within the sealed container 10, such gaseous contents are evacuated from the sealed container 10 through the apertures 72 in the gas conduits 70 and 71, the fitting 32, the body 94 and the conduit 108 to suitable test equipment.

An alternate embodiment of the gas fitting and gas conduits is shown in FIG. 7. In this embodiment, the gas fitting 110 is constructed in substantially the same manner as the fitting 32 described above, with the exception that the spacing between the four gas flow ports is altered. As shown in FIG. 7, the spacing between the gas flow ports in each pair of gas flow ports is smaller than that illustrated in FIG. 4 so as to form an elongated, substantially three-sided shape in the gas flow conduits 112 and 114. This shape for the gas conduits 112 and 114 is particularly suited for use in elongated, substantially rectangular, sealed containers.

Figure 8:
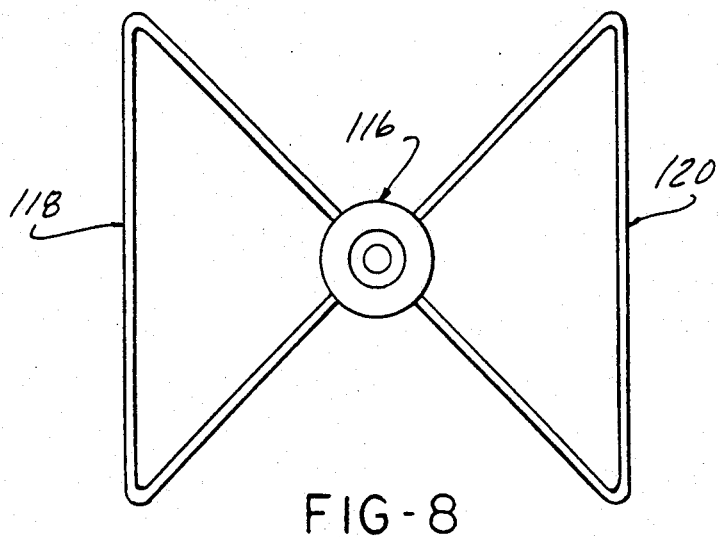
FIG. 8 is a plan view of another embodiment of the fitting and tube apparatus of the present invention.

Another embodiment is shown in FIG. 8 in which the spacing between the gas flow ports in each pair of ports is greater than that described above and illustrated in FIG. 4. This forms a generally triangular shape for the gas conduits 118 and 120 for use in substantially square-shaped sealed containers.

In summary, there has been disclosed a unique sealed gas emission container and a fitting and tube apparatus for a sealed gas emission container which overcomes certain deficiencies in such previously devised devices. The fitting and tube apparatus has a smoothly curved shape with a minimum height so as to prevent the formation of wrinkles and dead spots within the interior of the sealed container when the sealed container is evacuated of gaseous contents. Further, the smooth shape of the fitting enables the sealed container to expand to a known, constant volume so as to provide accurate tests on the gaseous contents stored within the sealed container.

The gas flow ports formed in the fitting are provided in a predetermined angular configuration to enable specified shapes of the gas conduits attached to the gas flow ports to be formed such that the gas conduits fill a substantially large portion of the sealed container. This provides proper inflation of the sealed container to a known, constant volume, as well as enabling the gases stored within the sealed container to be withdrawn from all portions of the sealed container to provide an accurate mixing of such gases for accurate test results.

The sealed container may be formed of single-ply top and bottom sheets which are sealed at their peripheral edges. Alternately, the sealed container may be formed of overlapping pairs of top and bottom sheets of thinner thicknesses which are also sealed at their peripheral edges.

What is claimed is:

1. A stand alone gas emission sample container for receiving, storing and discharging a constant volume of gas emissions, the container comprising:
   first and second pairs of flexible plastic sheets, each of the first and second pairs of sheets being formed of at least first and second separate sheets disposed in overlapping relationship with each other;
   means for sealingly joining the first and second pairs of sheets only along the entire peripheral edges of the first and second pair of sheets to form a hollow, expandable, sealed cavity of a predetermined constant volume between the inner most facing sheets of the first and second pairs of sheets;
   each of the first and second sheets of the first and second pairs of sheets being formed of a gas impervious, chemically inert material;
   aligned apertures formed in a predetermined position in the first and second sheets of one of the first and second pairs of sheets; and
   gas flow fitting means, sealingly mounted on and extending through the aligned apertures in the one of the first and second pairs of sheets into fluid flow communication with the hollow cavity, for forming a gas flow path to the hollow cavity to store a constant volume of gas emissions in the hollow cavity and for discharging the constant volume of gas emission from the hollow cavity.

2. The container of claim 1 wherein:
   all of the at least first and second sheets of the first and second pairs of sheets are formed of an identical material.

3. The container of claim 1 wherein the means for sealingly joining comprises:
   first and second spaced heat seams, each extending completely around the peripheral edges of the first and second pairs of sheets.

* * * * *